US011684293B2

(12) United States Patent
Slepian

(10) Patent No.: US 11,684,293 B2
(45) Date of Patent: Jun. 27, 2023

(54) SENSORS AND METHOD FOR DEFINING BREATHING SIGNATURES FOR IDENTIFYING RESPIRATORY DISEASE

(71) Applicant: Arizona Board of Regents on Behalf of the University of Arizona, Tucson, AZ (US)

(72) Inventor: Marvin J. Slepian, Tucson, AZ (US)

(73) Assignee: Arizona Board of Regents on Behalf of the University of Arizona, Tucson, AZ (US)

(*) Notice: Subject to any disclaimer, the term of this patent is extended or adjusted under 35 U.S.C. 154(b) by 258 days.

(21) Appl. No.: 17/116,157

(22) Filed: Dec. 9, 2020

(65) Prior Publication Data

US 2021/0169375 A1   Jun. 10, 2021

Related U.S. Application Data

(60) Provisional application No. 62/945,866, filed on Dec. 9, 2019, provisional application No. 62/945,711, filed on Dec. 9, 2019.

(51) Int. Cl.
*A61B 5/113* (2006.01)
*A61B 5/091* (2006.01)
(Continued)

(52) U.S. Cl.
CPC ............ *A61B 5/113* (2013.01); *A61B 5/0004* (2013.01); *A61B 5/0077* (2013.01); *A61B 5/05* (2013.01);
(Continued)

(58) Field of Classification Search
CPC ......... A61B 5/113; A61B 5/389; A61B 5/004; A61B 5/0077; A61B 5/05; A61B 5/087;
(Continued)

(56) References Cited

U.S. PATENT DOCUMENTS 10,702,166 B1*   7/2020   Freeman .............. A61B 5/0803
10,709,414 B1*   7/2020   McLane ................ G16H 40/63
(Continued)

*Primary Examiner* — Linda C Dvorak
*Assistant Examiner* — Abigail Bock
(74) *Attorney, Agent, or Firm* — Cozen O'Connor

(57) ABSTRACT

A lung function analysis system includes motion sensing devices each including accelerometers, gyros, battery, processor, and ireless transmitter, the processor configured to read motion data from the accelerometers and gyros and transmit the motion data over the wireless transmitter. The system includes a data collection device receiving the motion data and recording the motion data in a database; and a computing device with a lung function data analysis routine adapted to analyze the motion data to provide information useful in treating pulmonary disease. In embodiments, the lung function analysis routine includes a classifier trained on a database of motion data and diagnoses. In embodiments, the accelerometers and gyros are three-axis and/or the devices include electromyographic sensors. In embodiments, the system includes remote sensors such as a stereo camera with or without markers, millimeter-wave radar, or an ultrasonic echolocation device. In embodiments the information produced may include FEV1, FVC, FEV1/FVC and FEF25/75.

11 Claims, 6 Drawing Sheets

(51) Int. Cl.
  *A61B 5/087* (2006.01)
  *A61B 5/00* (2006.01)
  *A61B 5/11* (2006.01)
  *A61B 5/107* (2006.01)
  *A61B 5/05* (2021.01)
  *A61B 8/08* (2006.01)
  *A61B 5/389* (2021.01)
(52) U.S. Cl.
  CPC .............. *A61B 5/087* (2013.01); *A61B 5/091* (2013.01); *A61B 5/1077* (2013.01); *A61B 5/1079* (2013.01); *A61B 5/1128* (2013.01); *A61B 5/389* (2021.01); *A61B 5/6823* (2013.01); *A61B 5/7267* (2013.01); *A61B 8/08* (2013.01); *A61B 2560/0214* (2013.01); *A61B 2562/0219* (2013.01); *A61B 2562/06* (2013.01)

(58) Field of Classification Search
  CPC ..... A61B 5/091; A61B 5/1077; A61B 5/1079; A61B 5/1128; A61B 5/6823; A61B 5/7267; A61B 8/08; A61B 2560/0214; A61B 2562/0219; A61B 2563/06
  See application file for complete search history.

(56) References Cited

U.S. PATENT DOCUMENTS

| | | | |
|---|---|---|---|
| 2018/0140252 A1* | 5/2018 | Luxon | A61B 5/4884 |
| 2019/0133499 A1* | 5/2019 | Auerbach | A61B 5/1135 |
| 2021/0113099 A1* | 4/2021 | Rogers | A61B 5/4803 |
| 2021/0259563 A1* | 8/2021 | Tadi | G01P 13/00 |

* cited by examiner

SENSORS AND METHOD FOR DEFINING BREATHING SIGNATURES FOR IDENTIFYING RESPIRATORY DISEASE

CLAIM TO PRIORITY

The present application claims priority to United States Provisional Patent Applications 62/945,866 and 62/945,711, both filed 9 Dec. 2019. The entire contents of the aforementioned provisional patent applications are incorporated herein by reference.

FIELD

The present application relates to the field of lung function monitoring devices, such as are useful in monitoring and treating asthma, chronic obstructive pulmonary disease (COPD), and other pulmonary disorders of humans and other mammals.

BACKGROUND

Classical lung function testing in humans includes testing for the lung function parameters forced vital capacity (FVC), which is defined as the quantity of air that can be exhaled forcibly after taking a full inhalation, and forced expiratory volume in one second (FEV1), a measure of the volume of air exhaled in one second following a deep inhalation. FEV1 and FVC are of interest in monitoring COPD and asthma because obstructions or other limitations in expiratory airflow caused by these conditions, and measurable as changes in FVC and FEV1, make breathing difficult, cause audible wheezing, and produce other symptoms. FEV1 and FVC measurements of patients suffering from other diseases, such as pneumoconiosis or silicosis, or recovering from pneumonia, may also be useful to physicians. Patients may therefore benefit from home lung function parameter monitoring, particularly if recovering from an attack or recent hospitalization; outpatient monitoring would be useful to assure functional improvement and avert recurrence necessitating repeat hospitalization. Similarly monitoring patients with chronic conditions, or monitoring while they undertake their daily activities, or exercise, to guide these activities or modulate adjunctive pharmacology would be useful.

Asthma signs and symptoms, including FVC and FEV1, vary from day to day or from week to week because asthma may be triggered by environmental conditions including pollens, medications, foods, environmental airborne contaminants and fumes, or breathing cold air, as well as exercise and common viruses and bacteria. Asthma is often treated with medications including short-acting beta agonists and longer-acting "controller" medications; patients having frequent variations in symptoms, including frequent asthma attacks, may need adjustment in prescribed medications as well as identification and avoidance of environmental triggers.

It is known that the human chest and abdominal walls typically move during breathing.

SUMMARY

In an embodiment, a lung function analysis system has multiple motion sensing devices, each motion sensing device includes at least one accelerometer, at least one gyroscope, a battery, a processor, and a wireless transmitter, the processor reads motion data from the accelerometer and gyroscope and transmit it over the wireless transmitter. The system also has a data collection device adapted to receive motion data from motion sensing devices and records the motion data in a database; and a workstation with a lung function data analysis routine that analyses the motion data to provide information useful in treating pulmonary disease.

In an embodiment, a method of obtaining information useful in treating pulmonary disease in a subject includes placing multiple motion sensing devices on the subject, each motion sensing device with at least one accelerometer, at least one gyroscope, a battery, a processor, and a wireless transmitter, the processor configured to read motion data from the accelerometer and gyroscope and to transmit it over the wireless transmitter. The method also includes collecting the motion data from the plurality of motion sensing devices with a digital radio; and analyzing the motion data to determine the information useful in treating pulmonary disease.

In another embodiment, a lung function analysis system includes a chest movement monitoring system comprising remote-sensing sensors and a processor, the processor configured to read sensor data from the remote sensing sensors and to determine chest and abdominal movements of a subject; and a workstation configured with a lung function data analysis routine adapted to analyze chest and abdominal movement data from the database to provide information useful in treating pulmonary disease.

DETAILED DESCRIPTION OF THE EMBODIMENTS

Data Acquisition System

Figure 1:
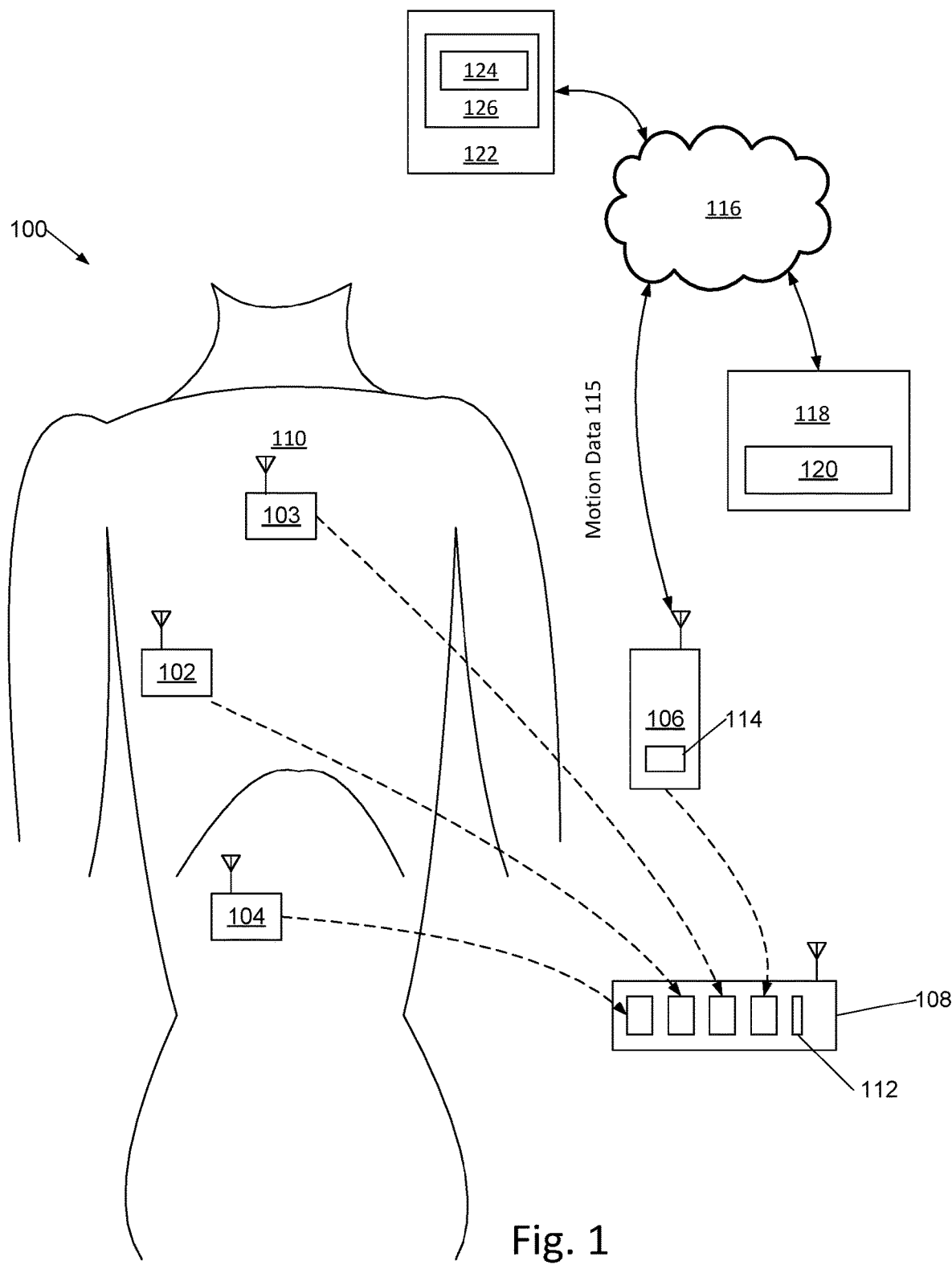
FIG. 1 is a block diagram of one example system for recording chest and abdominal movement data from which lung function data is derived, in embodiments.

A system 100 for collecting chest and/or abdominal wall movement information includes one or more "biostamp" sensor devices 102, 103, 104, (FIG. 1) such as, but not limited to, the Biostamp nPoint manufactured by MC10, Inc., 10 Maguire Rd., Building 3, Floor 1, Lexington, Mass. 02421. Alternative sensor devices capable of being attached to a subject that contain accelerometers and gyroscopic sensors for sensing motion of the subject are referred to herein as biostamp sensor device. Each biostamp sensor device is a portable, lightweight, motion-sensing device configured to be attached to skin of a subject 110 using an adhesive. Sensor devices 102, 103 and 104 may communicate wirelessly with cell phone 106. When not in use, sensor devices 102, 103 and 104 may be placed in charging device 108, as shown by dashed lines and described in more detail below.

Figure 2:
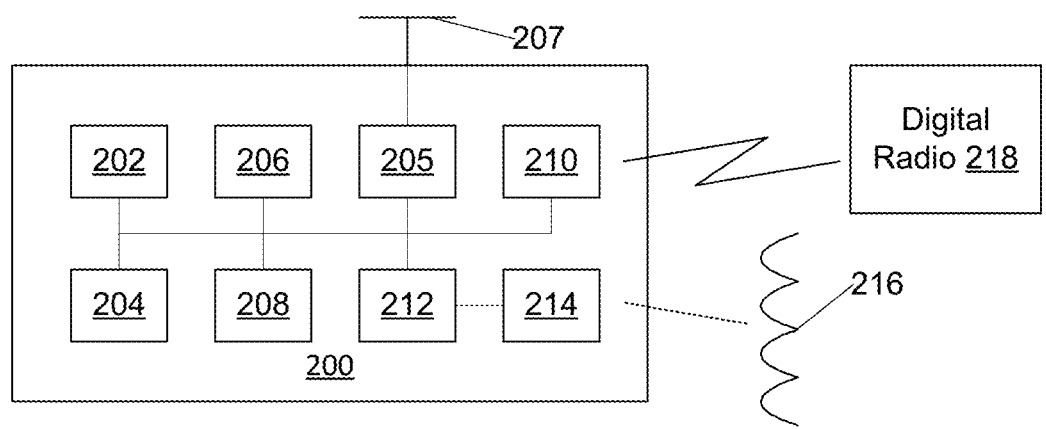
FIG. 2 is a block diagram of a biostamp data-collection stick-on device, in embodiments this may be the Biostamp nPoint® (Trademark of MC10, Inc, Lexington, Mass.) device.

As shown in FIG. 2, each biostamp sensor device 200 includes three-axis accelerometers 202 and three-axis gyroscopes 204 adapted to sense motion, a single-channel analog voltage sensor 205 with a surface electrode 207 for sensing electromyographic signals, the analog voltage sensor 205 and electrode 207 together forming an electromyographic channel, a processor 206, a memory 208, a digital radio transceiver 210, a battery 212, and an inductive battery charger 214 adapted to charge the battery 212 when energized by AC magnetic fields from an external inductor 216 such as an inductor within charging station 108. In a particular embodiment the digital radio transceiver 210 is a Bluetooth radio configured to communicate wirelessly with modern cell phones 106 (FIG. 1) or other digital radio transceivers 218 that may or may not use Bluetooth) such as a digital radio of charging station 108. In an embodiment, three-axis gyroscopes 204 are three-axis rate gyroscopes.

The processor 206 of each biostamp sensor device is configured with firmware (not shown) in memory 208 to record motion data 115 derived from accelerometers 202, voltage sensor 205, and gyroscopes 204 and store this data in memory 208 until that recorded motion data can be confirmed as having been transmitted by digital radio transceiver 210 to a biostamp-associated app 114 in cell phone 106 or to charging station 108. Once received in cell phone 106, motion data 115 is accumulated and periodically retransmitted by cell phone 106.

In an alternative embodiment, the sensor devices being stretchable and further including a stretch sensor adapted to measure stretch of the sensor device. In this embodiment the processor 206 is configured to read the strain sensor and the motion data includes stretch data read from the strain sensor.

In embodiments, AC-powered charging station 108 is adapted to provide AC magnetic fields to charge biostamp sensor devices 102, 103, 104 when the biostamp sensor devices are not adhered to subject 110, to charge cell phone 106 when the cell phone is not being carried by subject 110, has a digital radio transceiver 218 adapted to communicate with biostamp sensor devices 102, 103, 104 that are docked with and charging in charging station 108, and a removable memory device 112. In an embodiment, charging station 108 is configured to use its digital radio transceiver 218 to copy motion data from biostamp sensor devices 102, 103, 104 into memory device 112 while the devices 102, 103, 104 are being charged.

Each biostamp device is configured with a unique identifier (not shown) that is transmitted with collected motion data so that data collected by sensor devices 102, 104, can be identified as motion data collected by particular sensor devices.

In an embodiment, biostamp-associated app 114 in cell phone 106 serving as a data collection device, the cell phone records motion data received from sensor devices 102, 103, 104, then uploads this motion data 115 through either a cellular data network wireless connection or an IEEE 802-11 "WiFi" wireless connection through the internet 116 onto a server 118 that stores the recorded motion data in a database 120. A physician may then access motion data from database 120 over internet 116 from a workstation 122 having a lung function data analysis routine 124 in memory 126; lung function data analysis routine 124 being configured to extract lung function information from motion data recorded in database 120.

In an alternative embodiment, charging station 108 serves as a data collection device receiving data from each biostamp device and records it in a database within memory device 112, the physician may then access the motion data from memory device 112 by moving memory device 112 into a connector of workstation 122, and execute lung function data analysis routine 124 on that collected motion data in the database of memory device 112.

In an alternative embodiment, instead of attaching stick-on sensors to the subject, "around body" or remote-sensing sensors are used to track and record body motions of subject 160 (FIG. 1A) from which chest and abdominal movements are determined. In an embodiment, at least two electronic cameras 156, 158 are positioned to record stereo image pairs of chest and abdomen of subject 160, the stereo image pairs being referenced herein as stereo images; in a particular embodiment markers 152, 153 are positioned on chest and markers 154 on abdomen of subject 160 so processor 162, using three-dimensional tracking routines in memory 164, can track chest and abdominal movements of subject 160, providing movement data corresponding to data from the 3-dimensional accelerometers and 3-dimensional gyroscopes of the biostamp sensor devices 102, 103, 104. In a particular embodiment, markers may be drawn on skin of the subject, or imprinted on an elastic garment worn by the subject 160. In another particular embodiment with improved three-dimensional tracing routines, no markers are necessary. In an alternative embodiment, a single camera is used with markers, the camera being moved between breaths and successive images are used to record the stereo image pairs.

In embodiments, the stereo images are used to extract three dimensional models of the chest and abdomen of the subject at multiple points during the subject's breathing cycle, differences between the three-dimensional models being used to determine changes in chest and abdomen volume during the breathing cycle and to thereby determine airflow.

Figure 1A:
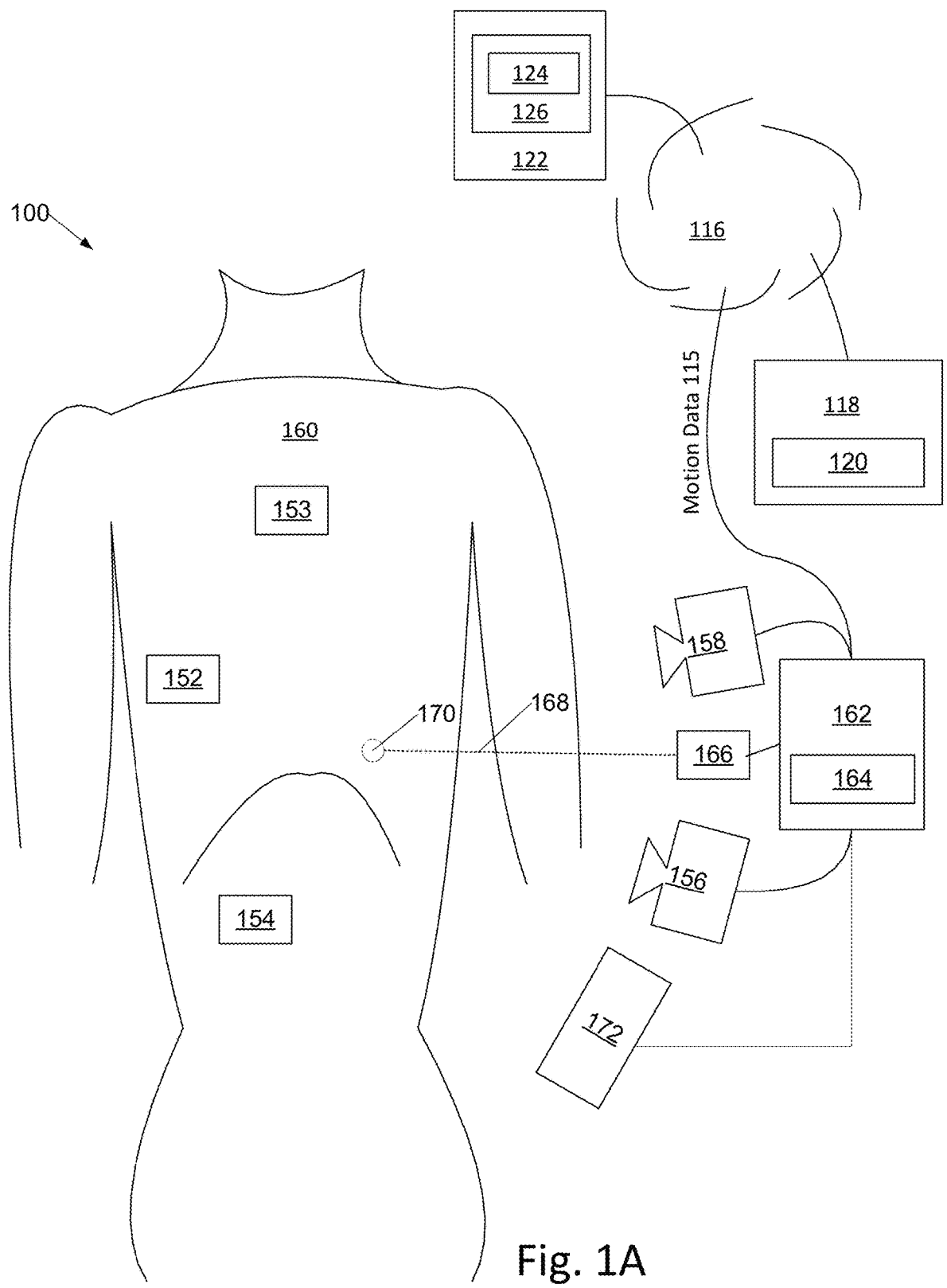
FIG. 1A is a block diagram of one example system for recording chest and abdominal movement using remote sensing using sensors deployed around a subject's body, in embodiments.
Figure 8:
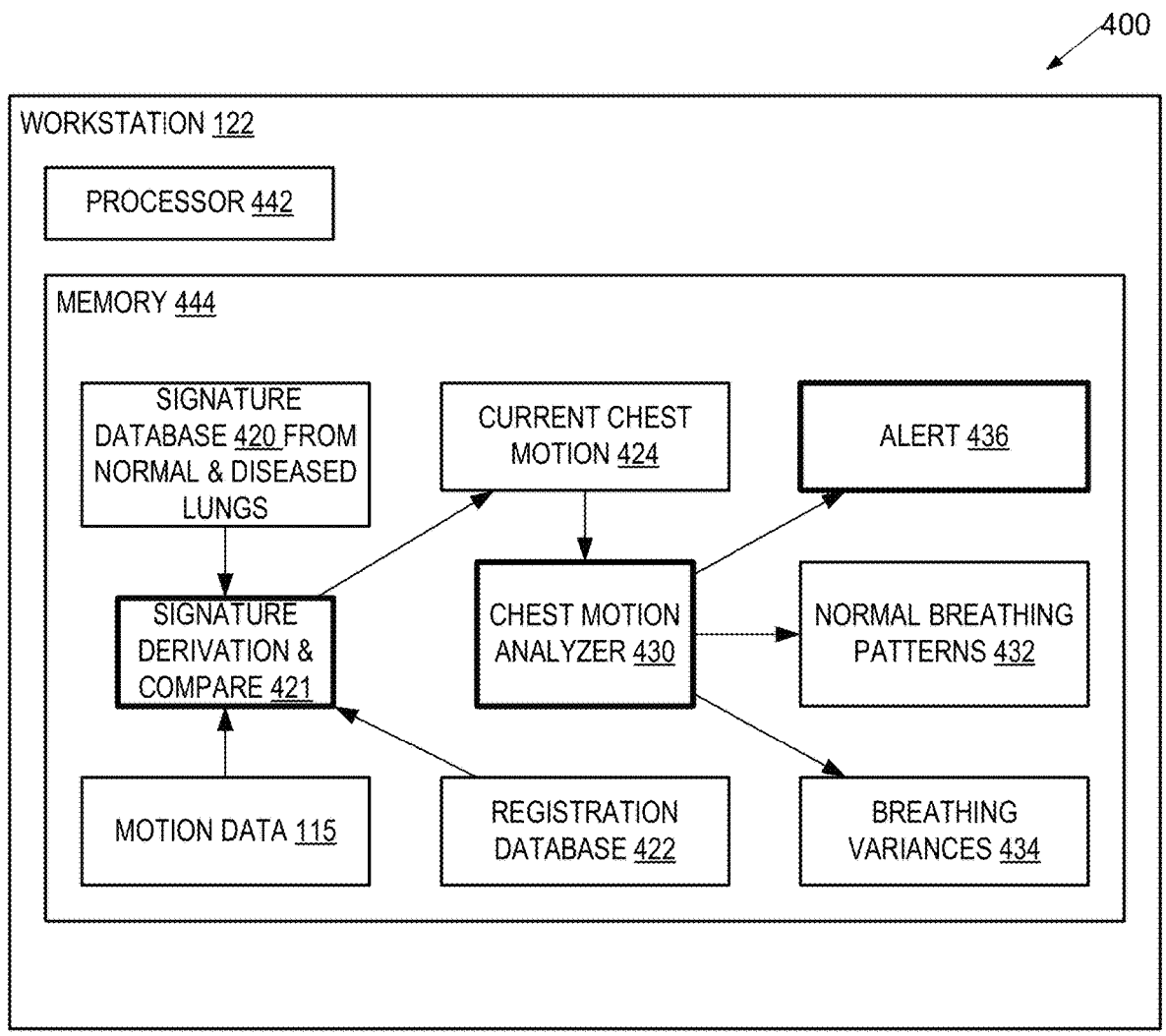
FIG. 8 is a block diagram of an analysis workstation adapted to process collected chest movement data.

In an alternative embodiment, the biostamp sensors described with reference to FIG. 1 are combined with the remote sensors of FIG. 1A, with movement data from both the 3-dimensional accelerometers and 3-dimensional rate gyroscopes of the biostamp devices and the movement data from the three-dimensional tracking routines of processor 162 being combined into overall chest movement data that may be uploaded to movement database 120 for processing by signature extraction and comparison module 421 (FIG. 8).

In another remote-sensing embodiment, cameras 156, 158 provide stereo pairs of images of chest and abdomen of subject 160 and processor 162 uses three-dimensional surface model extraction routines in memory 164 to construct a three-dimensional surface model of subject 160. In a particular embodiment three dimensional models are constructed from stereo image pairs after the subject's inhaling but prior to exhaling, after one second of exhaling, and after complete exhalation by the subject; volume changes during exhalation provide a direct measure of FEV1 and FVC that can be correlated directly to spirometry results.

In another remote-sensing embodiment, a laser beam 168 is repeatedly scanned across subject 160 by scanning laser 166, intersection 170 of the laser beam with the subject is imaged by an electronic video camera 158. Processor 162, knowing positions of camera 158 and laser 166 and the angle of beam 168 at each frame of video captured by camera 158, can determine position of the intersection 170 in three dimensions and determine movements of chest and abdomen of subject 160 effectively tracking motion of subject with lidar.

In another remote-sensing embodiment, ultrasonic transducers 172 are positioned to track position of chest and abdomen of subject 160 by ultrasonic echolocation and tracking of subject 160.

In another remote-sensing embodiment, a radar mapping system using millimeter-wavelength electromagnetic radiation is used to image skin surface of subject 160 through any clothing worn by subject 160, in a manner resembling millimeter-wavelength scanning systems used at airports to inspect travelers; images derived from the radar mapping system are processed by processor 162 to determine movements of chest and abdomen of subject 160.

In all remote-sensing embodiments herein described, processor 162 is configured to upload motion data 115 through a computer network that may be the internet 116 onto server 118 and stored in database 120, where the data may be accessed as describe with respect to the embodiment of FIG. 1.

Lung Function Measurements

Figure 3:
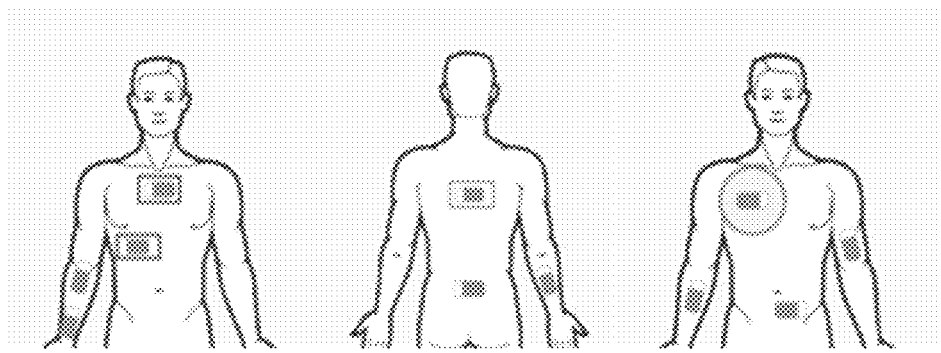
FIG. 3 is an illustration of example data collection device placements on experimental subjects.
Figure 4:
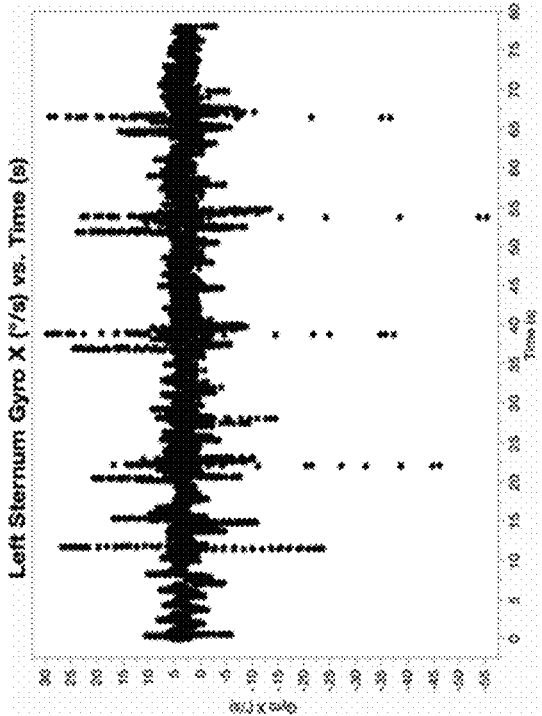
FIGS. 4, 5, 6, and 7 are plots of motion data versus time for data collection devices placed on right back, right hypochondrium, sternum X, and sternum Y, respectively.
Figure 5:
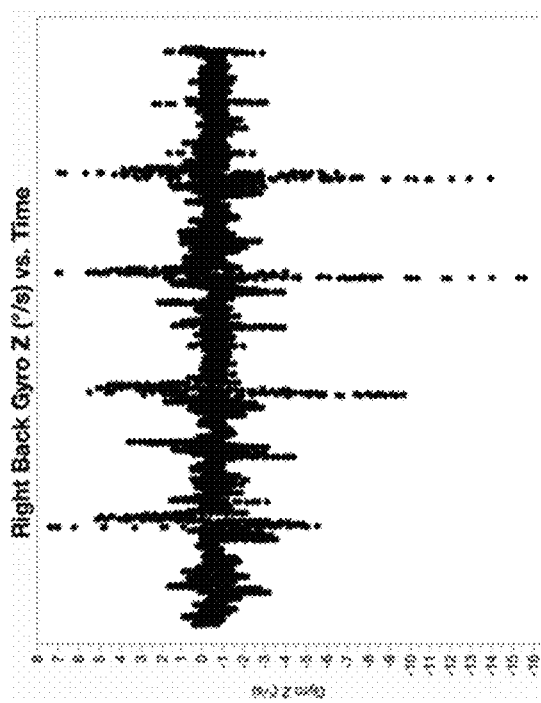
Figure 6:
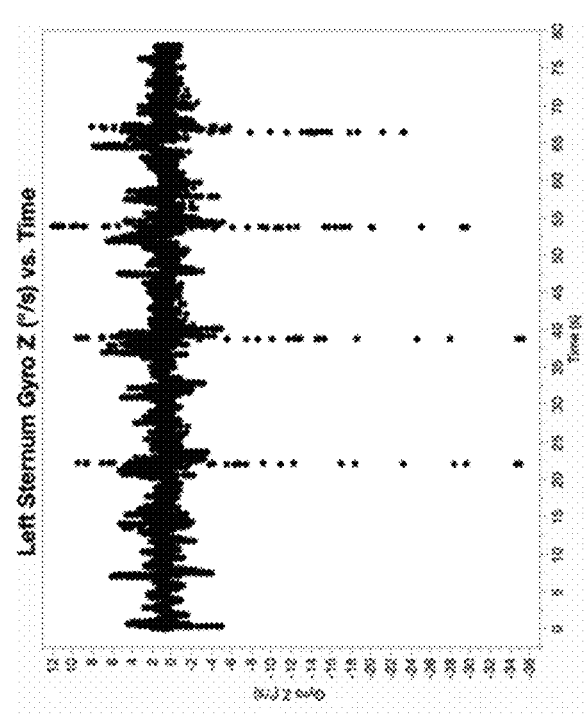
Figure 7:
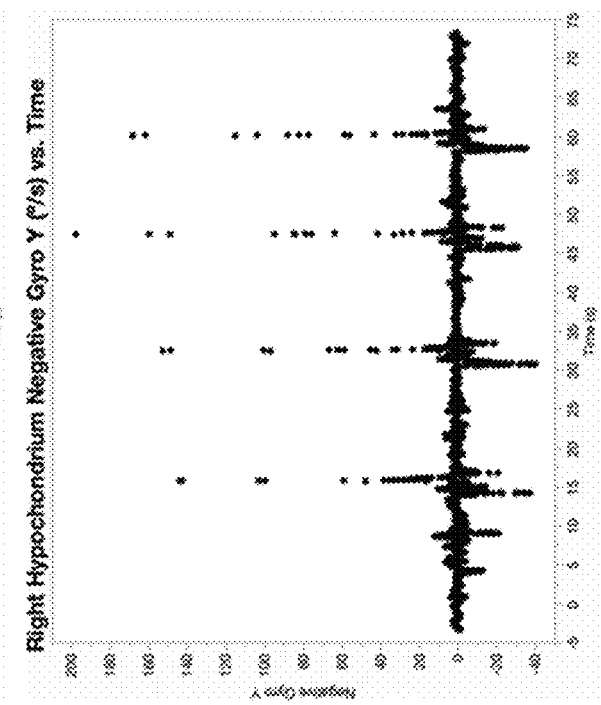

When biostamp sensor devices 102, 103, 104 are used for sensing lung function, one device 102 is attached to a chest wall of subject 110 over the right pectoral region, a second device 104 attached to an abdominal wall of subject 110 at the right hypochondrium, and a third device 103 is attached to subject 110 at the sternum. In embodiments, multiple devices are attached to subject 110 including one on the subject's back, as well as the sternal, back, right pectoral, and right hypochondrium body regions of subject 110 as shown in FIG. 3.

With biostamp sensor devices, signatures may be derived from recorded accelerations in 3 dimensions (X, Y, and Z) and angular movements (pitch, yaw, and roll) by integrating accelerations to get velocity and integrating again to get approximate chest positions. Signatures of normal breathing, exaggerated breathing, and breathing by those suffering from various lung diseases are correlated to FEV1 and FVC, determined via spirometry or other standardized pulmonary function test (PFT) methods, in experimental subjects to determine a calibration from which FEV1 and FVC can be estimated in additional subjects to obviate need for spirometry in the additional subjects. PFTs are also used to determine related parameters including tidal volume, vital capacity, maximal mid expiratory flow rate (MMEFR) or forced expiratory flow ($FEF_{25-75}$), and forced vital capacity.

In an alternative embodiment, an additional sensor device may be positioned on the subject's chest wall in a location where electrode 207 and voltage sensor 205 can detect electromyographic signals from intercostal muscles, data from the electromyographic signals is included as electromyographic data in the motion data transmitted by each sensor device and recorded in the database.

The metric that this project focused on detecting is Forced Vital Capacity (FVC). A reference value can be computed for FVC and Forced Expiratory Volume in one second (FEV1) based on a subject's age and sex. A subject's actual FVC and FEV1 are often measured by physicians, and an FEV1 to FVC ratio computed, to classify lung function impairment as follows in table 1:

TABLE 1

| SPIROMETRY TEST | NORMAL | ABNORMAL | |
|---|---|---|---|
| FVC and FEV1 | Equal to or greater than 80% | Mild<br>Moderate<br>Severe | 70-79%<br>60-69%<br>less than 60% |
| FEV1/FVC | Equal to or greater than 70% | Mild<br>Moderate<br>Severe | 60-69%<br>50-59%<br>less than 50% |

Once measured, subjects having abnormally low FVC or low FEV1/FVC ratios may be treated with inhaled and/or systemic medications to improve their lung function; for example, but not limitation, asthma, where the FEV1/FVC ratio is often particularly low during "attacks", may be treated with inhaled or systemic steroids, beta agonists or anticholinergics—e.g. ipratropium and tiotropium, and treatment is often monitored by observing changes in FEV1/FVC.

This study defines and detects a digital 'signature' of breathing which correlates with FVC, utilizing multiple multimodal biosensors on various locations on the body to measure movement during breathing. Oftentimes, health professionals are interested in FEV1/FVC instead of just FVC. When compared to the reference value, a lower measured value corresponds to a more severe lung abnormality. As reference, FVC ranges for normal and abnormal lung performance are displayed in Table 2 where obstruction and restriction represent broad classifications of lung disease.

TABLE 2

| | Normal | Obstruction | Restriction | Mixed/combined |
|---|---|---|---|---|
| $FEV_1$ | >80% predicted | > or <80% predicted | <80% predicted | <80% predicted |
| FVC | >80% predicted | >80% predicted | <80% predicted | <80% predicted |
| $FEV_1$/FVC or $FEV_1$/VC (depending on which is higher, FVC or VC) | >70% | <70% | >70% | <70% |

Results suggest that there is a correlation between the kinetic data and FVC. In FIGS. 4-7, each deep exhalation the subject performed is visible as each of the spikes, and the amplitude of each spike loosely correlated with FVC for all subjects tested.

Using biostamp, or equivalent, sensor devices around the thorax of a patient may be a viable method of measuring lung performance data, with each breath easily visible in data (See FIG. 4-7)—each spike is one breath, and large breaths such as an extremely forceful exhale, as is required for accurately measuring FVC and FEV1, showing pronounced spikes in motion data. Many different locations on the thorax result in visible results, meaning that different sensor placements may optimize measurement accuracy for each particular disorder studied in this way.

Trials with subjects with specific lung disorders are used to generate a training database, this training database is then used to train analysis and classifier routines for lung function data analysis routine 124 to diagnose respiratory or other illnesses. Large-scale trials utilizing this novel multi-modal sensor technology will require adapting big-data technologies, machine learning, and artificial intelligence to process the sheer quantity of data produced, and to extract actionable intelligence for healthcare professionals.

Data Analysis and Signature Processing

In an embodiment, FIG. 8 shows one exemplary system 400 for processing motion data 115 (FIG. 1) operable on workstation 122 by using a breathing signature database 420 containing signatures of chest and abdomen motion data derived from subjects with diseased and normal lungs, as well as prior motion data from the same subject 110 from which motion data is currently being analyzed. System 400 thereby determines the chest motion activity of subject 110 without other input. System 400 includes a signature extractor and comparison module 421 that processes motion data against signatures within breathing signature database 420 to determine current chest motion data 424 that defines the activity being performed by subject 102.

A registration database 422 correlates the location of each biostamp sensor device 102, 103, 104 on subject 110. For example, registration database 422 may define that sensing device 102 is positioned on a right chest of subject 110

Workstation 122 uses signature extraction and comparison module 421, implemented as machine readable instructions stored within memory 444 and executed by processor 442, to determine current chest motion data 424 of subject 110. Signature extraction and comparison module 421 processes sensor data against a breathing signature database 420 (FIG. 8) in memory 126 and generates current chest motion data 424 that defines the identified activities being performed by subject 110. Breathing signature database 420 may represent "Big data" and may include signatures corresponding to breathing of many subjects. A signature extraction and comparison module of chest motion analyzer 430 thereby matches signatures derived from sensor data to signatures defined within database 420 to determine breathing related current chest motion data 424 of subject 110 and analyze the chest motion in chest motion analyzer 430 to determine an FEV1/FVC ratio and, if chest motion breathing, and FEV1/FVC ratio matches normal breathing patterns 432 for that subject 110, abnormal warranting alerts 436, or simply variant activity 434.

Figure 9:
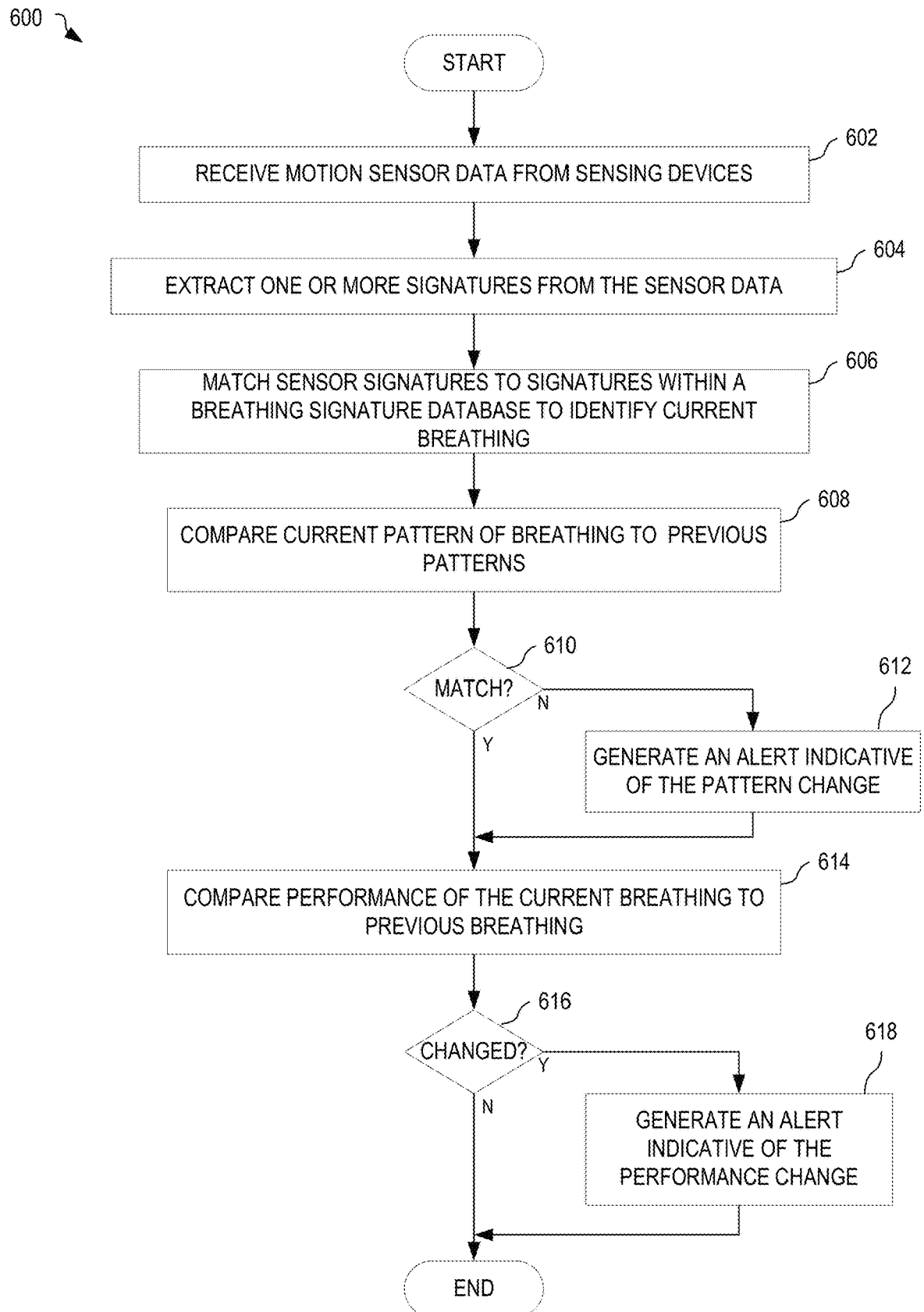
FIG. 9 is flowchart illustrating analysis of collected chest movement data.

FIG. 9 is a flowchart illustrating a method 600 for detecting change in breathing of subject 110 based upon chest motion. Method 600 is implemented within signature extraction and comparison module 421 and chest motion analyzer 430 of workstation 122 (FIG. 1).

In step 602, method 600 receives motion data 115 from the multiple biostamp sensors as configured with sensor placements. In step 604, method 600 extracts one or more signatures from the sensor data. In step 606, method 600 matches the sensor signatures of step 604 to signatures within a breathing signature database to identify a corresponding activity.

In step 608, method 600 compares a current pattern of activities to previous patterns of breathing. In one example of step 608, breathing analyzer 430 determines FVC and FEV1 together with an FEV1/FVC ratio and a breathing rate. In alternative embodiments, breathing analyzer determines flow rates such as Maximum Expiratory Flow (MEF), Forced Expiratory Flow from 25% to 75% of vital capacity (FEF 25-75), or Mixed Midexpiratory Flow Rate (MMFR) as additional or substitute measures of lung function.

Step 610 is a decision. If, in step 610, method 600 determines that the current pattern of breathing does not match the previous or expected pattern of breathing, method 600 continues with step 612; otherwise, method 600 continues with step 614. In step 612, method 600 generates an alert indicative of the pattern change. In one example of step 612, a breathing analyzer module of chest motion analyzer 430 generates alert 436 to indicate changes in the pattern of current breathing 424 as compared to previous patterns within normal breathing patterns 432. Method 600 then continues with step 614.

In step 614, method 600 compares performance of the current breathing to previous breathing. In one example of step 614, breathing analyzer module of chest motion analyzer 430 compares breathing performance defined by current chest motion data 424 to previous performances of the same activity within normal breathing patterns 432 to determine breathing variances 434.

Step 616 is a decision. If, in step 616, method 600 determines that there are changes, method 600 continues with step 618; otherwise, method 600 terminates.

In step 618, method 600 generates an alert indicative of the change breathing. Method 600 then terminates.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of obtaining lung function parameters comprising forced vital capacity (FVC), forced expiratory volume in one second (FEV1), tidal volume, vital capacity, maximal mid expiratory flow (MMEFR), forced expiratory flow ($FEF_{25-75}$), or forced vital capacity in a subject comprising:
    placing a plurality of motion sensing devices on the subject at the right pectoral region, a right hypochondrium region and a sternum, respectively, of the subject, each motion sensing device of the plurality of motion sensing devices comprising at least one accelerometer, at least one gyroscope, a battery, a processor, and a wireless transmitter, the processor configured to read motion data from the at least one accelerometer and the at least one gyroscope and to transmit the motion data over the wireless transmitter;
    placing at least two electronic cameras in a position to provide stereo images of a chest and abdomen of the subject;
    collecting the motion data from the plurality of motion sensing devices with a digital radio;
    constructing a three-dimensional surface model of subject using three-dimensional surface model extraction routines on stereo image pairs from the at least two electronic cameras after the subject's inhaling but prior to exhaling, after one second of exhaling, and after complete exhalation by the subject; and
    analyzing the collected motion data and the three-dimensional model together to determine lung function parameters comprising FVC, FEV1, tidal volume, vital capacity, maximal mid expiratory flow (MMEFR), forced expiratory flow ($FEF_{25-75}$), or forced vital capacity.

2. The method of claim 1 wherein the at least one accelerometer is a three-axis accelerometer and the at least one gyroscope is a three-axis gyroscope.

3. The method of claim 1 further comprising using a classifier trained on a database of motion data and diagnoses to determine the lung function parameters comprising FVC, FEV1, tidal volume, vital capacity, maximal mid expiratory flow (MMEFR), forced expiratory flow ($FEF_{25-75}$), or forced vital capacity.

4. The method of claim 2 wherein each motion sensing device of the plurality of motion sensing devices further comprise an electromyographic channel and wherein the motion data further comprises data measured from the electromyographic channel.

5. A lung function analysis system comprising:
   a chest movement monitoring system comprising:
      at least three motion sensors configured to be attached to a subject at a right pectoral region, a right hypochondrium region and a sternum of the subject, respectively, the at least three motion sensors further comprising at least one three-axis accelerometer, at least one three-axis gyroscope, a battery, a second processor, and a wireless transmitter, the second processor configured to read motion data from the at least one three-axis accelerometer and the at least one three-axis gyroscope and to transmit the motion data over the wireless transmitter;
      at least one electronic video camera configured to provide images of the subject;
      a laser repeatedly scanning a laser beam across the subject in an area captured by the electronic video camera; and
      a processor configured to:
      read sensor data from the at least three motion sensors;
      process image frames captured by the electronic video camera to determine movement data of the subject by determining a position of an intersection between the laser beam and the subject in three dimensions;
   combine the sensor data and the movement data to determine chest and abdominal movements of a subject; and
      record chest and abdominal movements of the subject in a database; and
   a workstation configured with a lung function data analysis routine adapted to analyze chest and abdominal movement data from the database to correlate the motion data to lung function parameters of forced vital capacity (FVC) and forced expiratory volume in one second (FEV1).

6. The lung function analysis system of claim 5 wherein the at least one electronic camera configured to provide stereo images of the subject comprises at least two electronic cameras.

7. The lung function analysis system of claim 5 wherein the chest movement monitoring system comprises a millimeter-wave radar.

8. The lung function analysis system of claim 5 wherein the chest movement monitoring system comprises an ultrasonic echolocation device.

9. The lung function analysis system of claim 5 wherein the lung function data analysis routine comprises a classifier trained on a database of motion data and diagnoses to determine the lung function parameters comprising FVC, FEV1, tidal volume, vital capacity, maximal mid expiratory flow (MMEFR), forced expiratory flow ($FEF_{25-75}$), or forced vital capacity.

10. The lung function analysis system of claim 5 wherein the lung function data analysis routine comprises a classifier trained on a database of motion data and diagnoses to determine the lung function parameters of FVC, FEV1, tidal volume, vital capacity, maximal mid expiratory flow (MMEFR), forced expiratory flow ($FEF_{25-75}$), or forced vital capacity.

11. The lung function analysis system of claim 10 wherein the data analysis routine also analyzes chest and abdominal movement data from the database to correlate the chest and abdominal movement data to lung function parameters of Maximum Expiratory Flow (MEF), Forced Expiratory Flow from 25% to 75% of vital capacity (FEF 25-75), or Mixed Midexpiratory Flow Rate (MMFR).

* * * * *